United States Patent [19]

Krapes

[11] Plant 4,098

[45] Sept. 6, 1977

[54] CARNATION PLANT NAMED MATADOR

[75] Inventor: David A. Krapes, Arvada, Colo.

[73] Assignee: Denver Wholesale Florists Company, Denver, Colo.

[21] Appl. No.: 730,659

[22] Filed: Oct. 7, 1976

[51] Int. Cl.[2] ..... A01H 5/00

[52] U.S. Cl. ..... Plt./73

[58] Field of Search ..... Plt./73

*Primary Examiner*—Robert E. Bagwill

*Attorney, Agent, or Firm*—Chas. W. Rummler

[57] ABSTRACT

A new variety of carnation plant distinguished by its high production of dark red flowers of a medium size borne on very sturdy and long stems, by its vigorous and much branched growth habit, its continuous flowering from Spring through Fall, and its relatively long lasting quality as a cut flower.

1 Drawing Figure

BACKGROUND OF THE NEW PLANT

My new variety of carnation plant was discovered by me in the month of March, 1969 as a sport of the carnation variety DWF White No. 1 (unpatented) being grown in my greenhouse at Arvada, Colo., for the production of cut flowers. The dark red coloration of the flower caught my attention and because of its attractive size and shape, I took cuttings and reproduced this sport as a new carnation variety. Propagation of this new plant through many generations at Denver, Colo., has shown commercially advantageous features of growth and flower production which with the flower color hold true from generation to generation and appear to be firmly fixed. Commercial scale propagation of this new plant is now being carried on by means of cuttings at Denver, Colo.

DESCRIPTION OF THE DRAWING

My new carnation variety is illustrated by the accompanying photographic drawing which in full color shows a partially opened bud, a newly opened flower, and a fully opened bloom, the flower color shown being as nearly true as is reasonably possible to obtain by conventional photographic procedures.

DESCRIPTION OF THE NEW PLANT

The following is a detailed description of this new variety of carnation plant according to observations made in the Summer of 1976 of greenhouse plants grown at Denver, Colo., under conventional greenhouse practices and procedures.

THE PLANT

Origin: Sport.
Parentage: DWF White No. 1 (unpatented).
Classification:
- *Botanic.*—Dianthus caryophyllus.
- *Commercial.*—Carnation for cut flowers.

Form: Upright tall bush.
Height: About 135 cm.
Growth: Vigorous, sturdy and erect.
- *Rate of growth.*—14 weeks to flower.

Branching: 4 to 5 branches on a principal stem.
Foliage: Quantity — Abundant with more than 100 leaves.
- *Leaf size.*—Medium to large.
- *Shape of leaf.*—Lanceolate with acuminate apex and entire margin.

- *Ribs.*—A single prominent mid-rib.
- *Color.*—Upper side — Light blueish-green. Under side — Light green.
- *Petioles.*—None. Leaf is amplexicaul.
- *Leaflets.*—None.

THE BUD

Size: Large. Diameter — 26 mm. Depth — 40 mm.
Form: Urn-shaped.
Opening rate: 1 to 2 days.
Color:
- *When sepals divide.*—Light red.
- *When petals begin to unfurl.*—Dark red.

Sepals: Hooded over bud until they divide.
- *Shape.*—Lobed wide oval with pointed tip.
- *Attitude.*—Sepals stand up and remain erect with full opened bloom.
- *Color.*—Inside — Light whitish-green. Outside — Light blueish-green.

Calyx:
- *Size.*—Large.
- *Shape.*—Funnel-shaped.
- *Aspect.*—Smooth.
- *Splitting.*—Very rare — less than 1% of flowers.

Peduncle: Strong and erect.
- *Color.*—Light blueish-green.

THE FLOWER

Blooming habit: Continuous, Spring through Fall, and profusely during blooming season.
Size of bloom: Medium. Diameter — 80 mm. Depth — 55 mm.
Borne: Singly, on sturdy upright stems.
Shape: Flat upon opening becoming high centered as the blossom becomes fully opened.
Petalage: Number of petals — 81.
- *Arrangement.*—Alternate in a whorl.
- *Form.*—Fan shaped with undulate and serrated margin.
- *Texture.*—Soft.
- *Appearance.*—Satiny.
- *Color.*—Outer petals — Dark red with light red base. Inside petals — Dark red with greenish-white base. Reverse sides — Duller and lighter red color.

Petaloids: One, of sub-normal size.
- *Color.*—Light green.

Persistence: Petals hang on and dry.
Fragrance: None.
Lasting quality:
- *On plant.*—7 to 8 days.

REPRODUCTIVE ORGANS

Stamens:

*Anthers.*—Number — 14. Arrangement: Around the pistil.

*Filaments.*—Length — 12 to 15 mm. Color: White.

*Pollen.*—Color — Greyish-white.

Pistils: Number — 2.

*Styles.*—Length — 40 mm.

*Stigmas.*—Color — Pinkish red.

Ovaries: 4 lobes.

This variety of carnation plant has a distinct high crowned flower which, colorwise, is similar to CSU Red (unpatented) and Scania (unpatented). The new plant has longer and stronger flower stems and the blooms are larger in diameter and more symmetrical than Renegade (unpatented).

Although the new plant may have some bullheading in the Fall or early Spring, it will be less than is had by CSU Red or Scania, and if bullheading is not a problem, a grower would prefer this variety because the flower form is more attractive and the presentation is more attractive. Otherwise the new variety is similar in growth characteristics to its parent DWF White No. 1.

I claim:

1. A new and distinct variety of carnation plant substantially as herein shown and described, characterized by its distinct high crowned dark red flowers which are borne on long and sturdy stems, its profuse production of blossoms during its blooming period, and by its very small amount of bullheading.

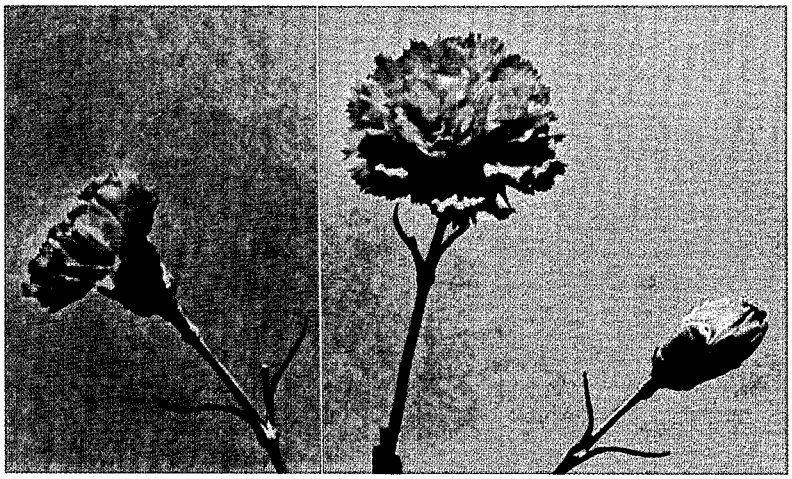

* * * * *